United States Patent [19]
Brinton et al.

[11] Patent Number: 5,997,911
[45] Date of Patent: Dec. 7, 1999

[54] COMPOSITION AND METHOD FOR REDUCING DIARRHEA IN POULTRY AND SWINE

[75] Inventors: Gene Brinton, Willmar; Jackie Brinton Mourning, New London, both of Minn.

[73] Assignee: Brinton Veterinary Supply, Inc., Willmar, Mo.

[21] Appl. No.: 08/703,638

[22] Filed: Aug. 27, 1996

[51] Int. Cl.$^6$ .......................... A61K 31/30; A61K 31/28; A61K 31/19; A61K 33/34

[52] U.S. Cl. .......................... 424/632; 424/617; 424/630; 424/631; 424/633; 424/634; 424/635; 424/637; 424/638; 424/646; 424/651; 424/657; 424/660; 424/661; 424/662; 424/715; 424/716; 424/717; 424/719; 514/499; 514/500; 514/557; 514/574; 426/2; 426/74; 426/532; 426/807

[58] Field of Search ..................................... 424/630–635, 424/637–638, 617, 646, 651, 657, 660–662, 715–717, 719; 514/499, 500, 557, 574; 426/2, 74, 532, 807

[56] References Cited

U.S. PATENT DOCUMENTS

| | | | |
|---|---|---|---|
| 2,333,950 | 11/1943 | Olsen et al. | 424/440 |
| 3,308,023 | 3/1967 | Russell | 514/197 |
| 3,895,116 | 7/1975 | Herting et al. | 514/557 |
| 4,053,477 | 10/1977 | Yen | 546/209 |
| 4,192,886 | 3/1980 | Towlerton et al. | 514/456 |
| 5,008,248 | 4/1991 | Bywater et al. | 514/23 |
| 5,100,647 | 3/1992 | Agus et al. | 514/286 |
| 5,248,505 | 9/1993 | Garwin | 514/63 |
| 5,494,481 | 2/1996 | Anderberg | 452/176 |

OTHER PUBLICATIONS

The Merck Index, 11$^{th}$ ed., Merck & Co., Inc., Rahway (NJ), 1989, p. 414.

The Merck Veterinary Manual. 7$^{th}$ ed., Merck & Co., Inc., Rahway (NJ), 1991, pp. 190–199.

Kabara, Jon J., "Food Grade Chemicals for use in Designing Food Preservatives Systems", Journal of Food Protection, vol. 44, 1981, pp. 633–647.

Primary Examiner—John Pak
Attorney, Agent, or Firm—Nikolai, Mersereau & Dietz, P.A.

[57] ABSTRACT

A composition and method for reducing the incidence of Poult Enteritis Mortality Syndrome in young turkeys, flushing in mature turkeys, and scours in swine. The composition of the present invention comprises, in combination, a simple copper (II) salt, a hydroxycarboxylic acid, and a buffering agent solubilized within the drinking water of turkeys and/or swine in an antidiarrheal effective dosage as preventative maintenance in avoiding the diarrheal conditions associated with PEMS, flushing, and scours. In a preferred embodiment, the simple copper (II) salt comprises copper sulfate pentahydrate, the hydroxycarboxylic acid comprises anhydrous citric acid, and the buffering, agent comprises ammonium carbonate.

28 Claims, No Drawings

COMPOSITION AND METHOD FOR REDUCING DIARRHEA IN POULTRY AND SWINE

BACKGROUND OF THE INVENTION

I. Field of the Invention

The present invention relates generally to a composition and method for reducing diarrhea in poultry and swine. More particularly, the present invention pertains to a composition and method for reducing the incidence of Poult Enteritis Mortality Syndrome (PEMS) in young turkeys, flushing in mature turkeys, and scours in swine. The composition comprises, in combination, a simple copper (II) salt, a hydroxycarboxylic acid, and a buffering agent solubilized within the drinking water of turkeys and/or swine in an antidiarrheal effective dosage as preventative maintenance in avoiding the diarrheal conditions associated with PEMS, flushing, and scours. In a preferred embodiment, the simple copper (II) salt comprises a copper sulfate pentahydrate, the hydroxycarboxylic acid comprises anhydrous citric acid, and the buffering agent comprises ammonium carbonate.

II. Discussion of the Prior Art

In recent times, diarrhea and related disorders have become an increasingly large threat to various populations of poultry and swine throughout the United States and abroad. Of heightened concern to veterinary scientists is the recent proliferation of Poult Enteritis Mortality Syndrome (PEMS). PEMS is an infectious, transmittable disease that typically affects young turkeys between 7 and 28 days of age and which is characterized by diarrhea, dehydration, weight-loss, anorexia, immunosuppression, growth depression (stunting) of greater than or equal to forty percent (40%), and mortality of greater than two percent (2%). Two clinical forms of PEMS exist. The first and most devastating form of PEMS is Spiking Mortality of Turkeys (SMT), which is characterized by a mortality rate greater than or equal to nine percent (9%) of the turkey population between 7 and 28 days of age, including at least three consecutive days with mortality greater than or equal to one percent (1%) of the turkey population. The second and more mild form of PEMS is Excess Mortality of Turkeys (EMT), which is characterized by a mortality rate greater than two percent (2%) of the turkey population between 7 and 28 days of age which does not equal or exceed one percent (1%) for three consecutive days.

PEMS was first reported in North Carolina in 1991 and has drawn considerable attention due to its ability to quickly decimate flocks and render surviving birds stunted such that they rarely reach market weight. The impact of PEMS on the North Carolina turkey industry has been estimated to have totaled approximately $34 million in losses in 1995 alone due to the concomitant high mortality rates and growth depression. The disease has subsequently appeared in additional states and threatens to wreak similar havoc on both the national and international turkey markets. PEMS is believed to be caused by a variety of infectious agents, including but not necessarily limited to enteropathogenic viruses, bacteria, and protozoa. The enteropathogenic viruses may include coronaviruses, birnaviruses, entero-like viruses, rotaviruses, and adenoviruses. The bacteria may include Salmonella, *E. coli*, Campylobacter, Bacteroides, and clostridia. The protozoa may include both cryptosporidia and Chochlosoma. The mode of transmission is fecal-oral and, alarmingly, the transmission to other poults can occur within 24–48 hours of exposure to the infectious agents. Following exposure, the rate of growth of the turkeys decreases and eventually ceases. After the growth rate stagnates, the body weight of the affected turkeys begins to decline and eventually plummets 4–8 days after exposure. It is this precipitous drop in body weight which is the main cause of PEM-induced turkey mortality. Turkeys which do survive PEMS, in addition to having less-than-normal body size, suffer an impaired immune system and an impaired ability to remove *E. coli* from the bloodstream.

Although the above-identified infectious agents are either known or suspected of being involved in PEMS, there is currently no validated diagnostic test for PEMS and therefore no ability to identify the particular infectious agents which are consistently involved with PEM outbreaks. Notwithstanding this lack of a diagnostic test, various control measures have been undertaken to prevent and/or mitigate the savagery of PEMS. One control measure designed to prevent the onslaught of PEMS involves decreasing the amount of moisture within the litter of the turkeys in an effort to minimize the degree to which the various infectious agents are able to culture within the litter. However, this litter dehydration technique typically requires the use of supplemental heat in addition to increased power ventilation, both of which can be prohibitively expensive to install and operate. Another preventative control measure entails sterilizing the physical environment where affected turkeys were previously maintained, including cleaning and disinfecting the actual pens between flocks. However, such activity has been only mildly effective in preventing the recurrence of high mortality of subsequent flocks and has had a negligible effect on the repeated incidence of growth depression or stunting. Various other preventative control programs which have been implemented and deemed not to be useful include the addition of oxygenated-chlorine disinfectants to the drinking water, increasing the temperature within the pens between broods, acidification of the drinking water, and the use of inactivated autogenous products or live vaccines approved for other species aimed at providing cross protection.

Other control efforts are designed to mitigate the damage after a particular turkey population has become infected with PEMS. The main thrust of these efforts is to keep the turkeys ingesting enough sustenance to carry them through the most devastating period of disease. One mitigating control method aims at supplementing the normal turkey feed with a variety of sweetening agents to entice the turkeys into eating. However, the addition of such sweetening agents, which may include molasses, whole rolled oats, powdered milk, and/or confectionary sprinkles, is disadvantageous in that it adds substantially to the difficulty and overall cost of feeding the turkeys. Related efforts entail replacing fine or mash feed with firm pellets of increased size so as to reduce the infectious agents' ability to grow and thrive within the food supply. Another mitigating control method involves periodically dumping the feed pans and/or cycling the feed lines to force the turkeys to get up and move about frequently. While this is believed to improve feeding activity among turkeys, it still requires a substantial amount of additional time and energy to effectuate and, thus, is disadvantageous from the standpoint of adding to the cost of feeding the turkeys. More importantly, the above-enumerated mitigating control measures have not been successful in adequately reducing the degree to which mortality and growth depression ravage flocks infected with PEMS.

Other diseases of heightened concern and great financial impact include flushing in older turkeys and scours in swine. Flushing is defined as any acute diarrheal disease affecting older turkeys, while scours is defined as any acute diarrheal disease affecting swine. The diarrheal conditions associated with both flushing and scours are particularly damaging to the turkey and swine industries, respectively, due to the attendant mortality and morbidity which accompanies each disease. Increased mortality rates are experienced within the affected turkey and swine populations due to the severe dehydration which typically accompanies diarrhea. The rate of incidence of the disease (morbidity) increases due to the profuise and watery defecation associated with diarrhea which creates exorbitantly wet litter conditions. The wet litter conditions, as will be appreciated by those skilled in the art, presents a suitable breeding ground for the infectious agents that cause flushing and scours, in addition to triggering other diseases and causing a host of other management problems.

Collectively, flushing and scours have afflicted the turkey and swine industry for years and, due to the aforementioned high mortality and morbidity, have consequently resulted in extremely large financial losses through time.

A need therefore a exists for a composition and method for preventing and/or mitigating the onslaught of Poult Enteritis Mortality Syndrome in young turkeys, flushing in older turkeys, and scours in swine. More particularly, the composition and method should be able to prevent and/or reduce the incidence of diarrhea, dehydration, weight-loss, anorexia, immunosuppression, growth depression, and mortality in turkeys and swine. The composition and method should also be inexpensive to implement and maintain and be capable of reducing the significant financial losses currently being incurred within the turkey and swine industry due to PEMS, flushing, and scours. In addition, the composition and method should be able to prevent and/or mitigate PEMS, flushing, and scours without the need for supplemental heating and ventilation systems. Furthermore, the composition and method should be equally effective in preventing the recurrence of high mortality and reducing the repeated incidence of growth depression in subsequent populations of turkeys and swine. The composition and method should also be capable of preventing and/or mitigating PEMS, flushing, and scours without the need for supplementing the food with sweetening agents, thereby reducing the difficulty and overall cost of feeding the turkeys. In similar fashion, the composition and method should not require periodically dumping the feed pans and/or cycling the feed lines to force the turkeys to get up and move about frequently, thereby minimizing the amount of time and energy required to feed the animals.

OBJECTS AND SUMMARY OF THE INVENTION

It is accordingly a principal object of the present invention to provide a composition and method for preventing and/or mitigating the onslaught of Poult Enteritis Mortality Syndrome in young turkeys, flushing in older turkeys, and scours in swine.

It is a further object of the present invention to provide a composition and method for preventing and/or reducing the incidence of diarrhea, dehydration, weight-loss, anorexia, immunosuppression, growth depression, and mortality in turkeys and swine stemming from PEMS, flushing, and/or scours.

A still further object of the present invention is to provide a composition and method for preventing and/or mitigating PEMS, flushing, and scours which is inexpensive to implement and maintain.

It is yet another object of the present invention to reduce the significant financial losses currently suffered by the turkey and swine industry due to PEMS, flushing, and scours.

It is still another object of the present invention to prevent and/or mitigate PEMS, flushing, and scours without the need for supplemental heating and ventilation systems.

It is a still further object of the present invention to provide a composition and method for preventing and/or mitigating PEMS, flushing, and scours which is equally effective in preventing the recurrence of mortality and reducing the repeated incidence of growth depression in subsequent populations of turkeys and swine.

It is yet another object of the present invention to provide a composition and method which is capable of preventing and/or mitigating PEMS, flushing, and scours without the need to supplement the food with sweetening agents.

It is still a further object of the present invention to a composition and method for preventing and/or mitigating PEMS, flushing, and scours which eliminates the need to periodically dump the feed pans and/or cycle the feed lines to make the turkeys and/or swine get up and move about frequently.

In accordance with the present invention, the foregoing objects and advantages are achieved by providing a veterinary composition for reducing diarrhea in poultry and swine, comprising, in combination, a simple copper (II) salt, a hydroxycarboxylic acid, and a buffering agent solubilized within the drinking water of the poultry and swine in an antidiarrheal effective dosage.

In accordance with another broad aspect of the present invention, the aforementioned objects are attained by providing a method of reducing diarrhea in poultry and swine, comprising the steps of: (a) providing approximately equal portions (weight) of a simple copper (II) salt and a hydroxycarboxylic acid along with a minor amount of a buffering agent; (b) dissolving the simple copper (II) salt, the hydroxycarboxylic acid, and the buffering agent in a quantity of water sufficient to produce a therapeutic veterinary solution; and (c) supplying the therapeutic veterinary solution to the drinking water of one of poultry and swine at a therapeutically effective rate.

In accordance with yet another broad aspect of the present invention, a method of preventing and/or mitigating the effects of PEMS, flushing, and/or scours is provided comprising the steps of (a) codissolving a simple copper (II) salt, a hydroxycarboxylic acid, and a buffering agent in water to produce a therapeutic veterinary solution; and (b) administering an antidiarrheal effective dosage of the therapeutic veterinary solution to the drinking water of one of poultry and swine.

Without limitation, the simple copper (II) salt may include one or more of copper sulfate pentahydrate, copper (II) halides, copper (II) acetate or any other simple copper (II) carboxylate, copper (II) acetylacetonate, copper (II) carbonate, copper (II) citrate, copper (II) lactate, copper (II) tartrate, copper (II) gluconate, copper (II) glycolate, copper (II) dilsopropylsalicylate, copper (II) tetrafluoroborate, copper (II) hexafluoroantimonate, copper (II) methoxide, copper (II) nitrate, copper (II) perchlorate, copper (II) thiocyanate, copper (II) trifluoromethanesulfonate, copper (II) molybdate and tungstate. Additionally, the simple copper (II) salt may include any number of simple copper (I) salts that upon dissolution in water under an atmosphere of air oxidize the copper (I) to the aforementioned copper (II) state.

Also by way of example and not limitation, the hydroxycarboxylic acid may include citric acid, lactic acid, propionic acid, malonic acid, gluconic acid, glutaric acid, oxalic acid, succinic acid, maleic acid, fumaric acid, ascorbic acid, sorbic acid, and tartaric acid. The hydroxycarboxylic acid may also include a hydroxyacid with α, β, γ, or δ substitution patterns. The hydroxycarboxylic acid may similarly comprise a hydroxyacid having a variable number of carboxylic acid and hydroxyl functional groups without departing from the scope of the present invention.

The buffering agent may include, but is not necessarily limited to, simple ammonium salts, simple carbonate salts, and a combination of a simple ammonium salt and a simple carbonate salt.

The simple ammonium salts may include ammonium chloride, while the simple carbonate salt may include sodium carbonate.

The foregoing features and advantages of the present invention will be readily apparent to those skilled in the art from a review of the following detailed description of the preferred embodiment in conjunction with the accompanying examples and claims.

DETAILED DESCRIPTION OF THE PREFERRED EMBODIMENT

Reference will now be made in detail to certain preferred embodiments of the present invention, examples of which are further illustrated in the following descriptive material.

The present invention comprises a composition and method for preventing and/or mitigating the onslaught of Poult Enteritis Mortality Syndrome (PEMS) in young turkeys, flushing in older turkeys, and scours in swine. In its broadest and most fundamental form, the veterinary composition of the present invention comprises, in combination, a simple copper (II) salt, a hydroxycarboxylic acid, and a buffering agent solubilized within the drinking water of turkeys and/or swine in an antidiarrheal effective dosage. As used herein, the term "antidiarrheal effective" means sufficient to achieve the desired therapeutic results in a majority of the subjects to which the veterinary composition of the present invention is administered. By reducing the incidence of diarrhea experienced by turkeys and swine, the veterinary composition effectively eliminates and/or minimizes the severe dehydration associated with PEMS, flushing, and scours. This advantageously increases the feed efficiency or feed conversion within the particular population of poultry and swine which, in turn, maximizes the effective rate of gain for the poults and swine. Maximizing the rate of gain is particularly important to the proper development of younger animals so that they are able to reach full weight for market.

In a preferred embodiment of the present invention, the simple copper (II) salt comprises copper sulfate pentahydrate, the hydroxycarboxylic acid comprises anhydrous citric acid, and the buffering agent comprises ammonium carbonate. Copper sulfate pentahydrate ($CuSO_4.5H_2O$), otherwise known as blue vitriol, bluestone, blue copperas, Roman vitriol, and Salzburg vitriol, is derived from the action of dilute sulfuric acid on copper or copper oxide and is generally in the form of blue crystals or blue crystalline granules or power which are readily soluble in water. Citric acid (2-hydroxy-1,2,3-propanetricarboxylic acid) is derived through mold fermentation of carbohydrates and comes in the form of colorless, translucent crystals or powder which are similarly water soluble. Ammonium carbonate (($NH_4$)$HCO_3$.($NH_4$)$CO_2NH_2$), otherwise known as crystal ammonia, ammonium sesquicarbonate, and hartshorn, is a water soluble mixture of ammonium bicarbonate and ammonium carbamnate obtained by subliming a mixture of ammonium sulfate and calcium carbonate.

As noted above, the antidiarrheal effective dosage of the veterinary composition of the present invention is the amount of a simple copper (II) salt, a hydroxycarboxylic acid, and a buffering agent which must be administered to the turkeys and/or swine via their drinking water in order to prevent a majority of the turkeys and/or swine from experiencing the diarrheal conditions associated with PEMS, flushing, and scours. In the preferred embodiment, the antidiarrheal effective dosage of the veterinary composition of the present invention is formed by codissolving approximately 216 grams of copper sulfate pentahydrate, approximately 216 grams of anhydrous citric acid, and approximately 21.6 grams of ammonium carbonate in a quantity of water sufficient to one liter and administering this solution to the drinking water of the turkey and/or swine at a therapeutically effective rate. As used herein, the term "therapeutically effective rate" is the rate at which the veterinary composition of the present invention is to be supplied to a particular turkey and/or swine population in order to prevent the onslaught of PEMS, flushing, and/or scours. For basic preventative maintenance on farms with no history of PEMS, flushing or scours, the therapeutically effective rate comprises 1 part veterinary composition to approximately 999 parts drinking water administered for a minimum of 50 percent of the time to a maximum of 100 percent of the time. On farms with a history of PEMS, flushing, or scours, the therapeutically effective rate comprises 1 part veterinary composition to approximately 511 parts drinking water administered for 100 percent of the time. Provided in the above-identified fashion, the veterinary solution of the present invention is particularly advantageous in preventing and/or minimizing the diarrheal conditions associated with PEMS, flushing, and scours.

The above-identified therapeutically effective rates are provided by way of example only and not limitation. To further explain, with the copper sulfate pentahydrate, anhydrous citric acid, and ammonium carbonate provided in the aforementioned amounts, the therapeutically effective rate for farms having a history of PEMS, flushing, or scours may range from a lower rate of 1 part veterinary solution to approximately 750 parts drinking water to an upper rate of 1 part veterinary solution to approximately 1000 parts drinking water, wherein the veterinary composition is supplied to the drinking water of the turkeys and/or swine at these volumetric rates for a minimum of 50 percent of the time to a maximum of 100 percent of the time. In similar fashion, the therapeutically effective rate for farms having a history of PEMS, flushing, or scours (with the copper sulfate pentahydrate, anhydrous citric acid, and ammonium carbonate provided in the amounts set forth above) may range from a lower rate of 1 part veterinary composition to approximately 250 parts drinking water to an upper rate of 1 part veterinary composition to approximately 750 parts drinking water, wherein the veterinary composition is supplied to the drinking water of the turkeys and/or swine at these volumetric rates for 100 percent of the time to effectively thwart the onslaught of the aforementioned enteric diseases.

Although the preferred embodiment of the present invention entails codissolving copper sulfate pentahydrate, anhydrous citric acid, and ammonium carbonate in water in the amounts specified above, it is to be understood that the effective amount of each component may range as follows without departing from the scope of the present invention. To be more specific, when dissolved in a quantity sufficient to one liter, the effective amount of copper sulfate pentahydrate may range between 113 and 340 grams thereof, the effective amount of anhydrous citric acid may range between 90 and 340 grams thereof, and the effective amount of ammonium carbonate may range between 2 and 68 grams thereof Under these particular specifications, then, the veterinary composition of the present invention may be prepared by codissolving between 113 and 340 grams of copper sulfate pentahydrate, between 90 and 340 grams of anhydrous citric acid, and between 2 and 68 grams of ammonium carbonate in a quantity of water sufficient to one liter. Thereafter, the veterinary composition may be administered to turkey poults and/or swine at the therapeutically effective rates set forth above to effectively prevent and/or combat PEMS in young turkeys, flushing in older turkeys, and scours in swine.

Various other compounds may be used as substitutes for copper sulfate pentahydrate, citric acid, and ammonium carbonate. To be more specific, the following copper (II) salts, hydroxycarboxylic acids, and buffering agents may be substituted for copper sulfate pentahydrate, citric acid, and ammonium carbonate, respectively, without departing from the scope of the present invention. The suitable substitutes for each are as follows:

Copper (II) Salts:
    Copper (II) Halides (including copper chloride, bromide, and iodide)
    Copper (II) Acetate
    Copper (II) Acetylacetonate
    Copper (II) Carbonate
    Copper (II) Citrate
    Copper (II) Lactate
    Copper (II) Tartrate
    Copper (II) Gluconate
    Copper (II) Glycolate
    Copper (II) Diisopropylsalicylate
    Copper (II) Tetraflouroborate
    Copper (II) Hexafluoroantimonate
    Copper (TI) Methoxide
    Copper (II) Nitrate
    Copper (II) Perchlorate
    Copper (II) Thiocyanate
    Copper (II) Trifluoromethanesulfonate
    Copper (II) Molybdate
    Tungstate
    Combinations of the Above Hydroxycarboxylic Acids:
    Homocitric Acid
    Lactic Acid
    Malonic Acid
    Propionic Acid
    Gluconic Acid
    Glutaric Acid
    Oxalic Acid
    Succinic Acid
    Maleic Acid
    Fumaric Acid
    Ascorbic Acid
    Sorbic Acid
    Tartaric Acid
    Combinations of the Above Buffering Agents:
    Ammnonium Chloride
    Sodium Carbonate
    Combinations of the Above The aforementioned substitute reagents for copper sulfate pentahydrate comprise simple copper (II) alkoxide, carboxylate, and mixed alkoxide-carboxylate salts of which there are many derivatives. However, it is to be noted with particularity that copper sulfate pentahydrate may also be replaced with any variety of simple copper (I) salts which, when dissolved in water under an atmosphere of air, oxidize to form one of the above-enumerated simple copper (II) salts. The above-identified substitute acid reagents comprise hydroxycarbolic acids and/or carboxylic acids. It should be noted, however, that the hydroxycarbolic acids may also include a hydroxyacid with $\alpha$, $\beta$, $\gamma$, or $\delta$ substitution patterns, in addition to hydroxyacids having variable numbers of carboxylic acid and hydroxyl functional groups. Lastly, the aforementioned substitute reagents for ammonium carbonate include simple ammonium salts, simple carbonate salts, and/or a combination of both.

EXAMPLE 1

A veterinary solution in accordance with a preferred embodiment of the present invention was formed dissolving the following compounds in a quantity of water sufficient to 1 liter.

|  | Grams | % of Total |
| --- | --- | --- |
| Copper Sulfate Pentahydrate | 216.0 | 47.62 |
| Citric Acid | 216.0 | 47.62 |
| Ammonium Carbonate | 21.6 | 4.76 |

To achieve the goals of preventing recurrent outbreaks of PEMS and flushing, the veterinary solution of the present invention was administered to turkeys from seven different farms having histories of PEMS and flushing as described below. A table containing data from these seven turkey farms is provided immediately below to evidence the benefit of administering the veterinary solution under the above-identified protocol. Specifically, Table 1 lists in chronological order the mortality rate for each flock of turkey within each farm leading up to the administration of the veterinary solution of the present invention (Pre-Administration Mortality) followed by the percent mortality for the first flock to which veterinary solution of the present invention was administered (Post-Administration Mortality). The Post-Administration Mortality rates were experienced after administering the veterinary solution at a rate of 1 part veterinary solution to approximately 511 parts drinking water in one hundred (100) percent of the drinking water supplied to the turkey poults from one week of age through twelve weeks of age. The size of each flock averaged between 15,000 to 20,000 turkeys/flock.

TABLE 1

| Farm Number | Flock Number | Percent Mortality |
| --- | --- | --- |
| 1 | 1 | 14.93% (Pre-Administration Mortality) |
|  | 2 | 21.25% (Pre-Administration Mortality) |
|  | 3 | 8.65% (Post-Administration Mortality) |
| 2 | 1 | 27.73% (Pre-Administration Mortality) |
|  | 2 | 5.86% (Post-Administration Mortality) |
| 3 | 1 | 25.09% (Pre-Administration Mortality) |
|  | 2 | 17.88% (Pre-Administration Mortality) |
|  | 3 | 16.69% (Pre-Administration Mortality) |

TABLE 1-continued

| Farm Number | Flock Number | Percent Mortality | |
|---|---|---|---|
|   | 4 | 8.69% | (Post-Administration Mortality) |
| 4 | 1 | 25.99% | (Pre-Administration Mortality) |
|   | 2 | 23.88% | (Pre-Administration Mortality) |
|   | 3 | 25.69% | (Pre-Administration Mortality) |
|   | 4 | 12.30% | (Post-Administration Mortality) |
| 5 | 1 | 23.64% | (Pre-Administration Mortality) |
|   | 2 | 20.47% | (Pre-Administration Mortality) |
|   | 3 | 6.41% | (Post-Administration Mortality) |
| 6 | 1 | 23.13% | (Pre-Administration Mortality) |
|   | 2 | 8.44% | (Post-Administration Mortality) |
| 7 | 1 | 14.93% | (Pre-Administration Mortality) |
|   | 2 | 15.98% | (Pre-Administration Mortality) |
|   | 3 | 7.60% | (Post-Administration Mortality) |

With reference to the foregoing, it can be readily appreciated that the incidence of mortality among young turkey poults was significantly decreased following the administration of the veterinary solution of the present invention in the manner described above. This translates into an increase in the percentage of turkeys which will be able to develop normally and reach full market weight. Based on the severe economic losses currently being suffered by the turkey industry due to PEMS and related illnesses, the aforementioned reduction in mortality rates obtainable through the administration of the veterinary solution of the present invention may readily save the turkey industry huge sums of money each year.

The veterinary solution of the present invention may also be used to prevent the onslaught of scours in swine on farms with no history of the disease by providing the veterinary solution at the therapeutically effective rate of 1 part veterinary solution to approximately 999 parts drinking water for between fifty percent (50%) and one hundred percent (100%) of the time. On farms with a history of scours, the veterinary solution of the present invention is capable of preventing recurrent outbreaks of the disease by administering the veterinary solution at the therapeutically effective rate of 1 part veterinary solution to approximately 511 parts drinking water for all of the drinking water supplied to the swine.

By way of summary, then, a veterinary composition for reducing diarrhea in poultry and swine is provided herein, comprising, in combination, a simple copper (II) salt, a hydroxycarboxylic acid, and a buffering agent solubilized within the drinking water of the poultry and swine in an antidiarrheal effective dosage. A method of preventing and/or mitigating the effects of PEMS, flushing, and/or scours is also provided comprising the steps of: (a) providing approximately equal portions (weight) of a simple copper (II) salt and a hydroxycarboxylic acid along with a minor amount of a buffering agent; (b) dissolving the simple copper (II) salt, the hydroxycarboxylic acid, and the buffering agent in a quantity of water sufficient to produce a therapeutic veterinary solution; and (c) supplying the therapeutic veterinary solution to the drinking water of one of the poultry and the swine at a therapeutically effective rate. In a preferred embodiment of the present invention, a method of preventing and/or mitigating the effects of PEMS, flushing, and/or scours is provided comprising the steps of: (a) codissolving a simple copper (II) salt, a hydroxycarboxylic acid, and a buffering agyent in water to produce a therapeutic veterinary solution; and (b) administering an antidiarrheal effective dosage of the therapeutic veterinary solution to the drinking water of one of poultry and swine.

In light of the foregoing, the present invention solves the various drawbacks found in the prior art. To be more specific, the present invention provides a composition and method for preventing and/or mitigating the onslaught of Poult Enteritis Mortality Syndrome in young turkeys, flushing in older turkeys, and scours in swine. The composition and method is capable of preventing and reducing the incidence of diarrhea, dehydration, weight-loss, anorexia, immunosuppression, growth depression, and mortality in turkeys and swine. The composition and method is also inexpensive to implement and maintain and is furthermore capable of reducing the significant financial losses currently being incurred within the turkey and swine industry due to PEMS, flushing, and scours. In addition, the composition and method is capable of preventing and mitigating PEMS, flushing, and scours without the need for supplemental heating and ventilation systems. The composition and method of the present invention is also equally effective in preventing the recurrence of high mortality and reducing the repeated incidence of growth depression in subsequent populations of turkeys and swine. Furthermore, the composition and method is capable of preventing and/or mitigating PEMS, flushing, and scours without the need for supplementing the food with sweetening agents, thereby reducing the difficulty and overall cost of feeding the turkeys. Lastly, the composition and method of the present invention does not call for the periodic dumping of the feed pans and/or the cycling of the feed lines, which thereby minimizes the amount of time and energy required to feed the animals.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself For example, it is to be understood that the above-enumerated manner of providing the veterinary composition of the present invention in an antidiarrheal effective dosage is provided by way of illustration and not limitation and that an antidiarrheal effective dosage may be obtained in one of several ways without departing from the scope of the present invention. To be more specific, an antidiarrheal effective dosage of the veterinary composition of the present invention may be obtained by decreasing the amount of simple copper (II) salt, hydroxycarboxylic acid, and buffering agent codissolved within a quantity of water sufficient to one liter and thereafter increasing the rate at which the solution is provided to the turkeys and/or swine. In similar fashion, it may be possible to provide an antidiarrheal effective amount of the veterinary composition of the present invention by increasing the amount of simple copper (II) salt, hydroxycarboxylic acid, and buffering agent codissolved within a quantity of water sufficient to one liter and thereafter decreasing the rate at which the solution is provided to the turkeys and/or swine.

What is claimed is:

1. A veterinary composition for reducing the incidence and magnitude of diarrhea related disorders in poultry and swine, said veterinary composition comprising, in combination, a simple copper (II) salt, a hydroxycarboxylic acid, and a buffering agent solubilized within the drinking water of said poultry and swine in a therapeutically effective dosage.

2. The veterinary composition as set forth in claim 1 and further, wherein said simple copper (II) salt comprises copper sulfate pentahydrate.

3. The veterinary composition as set forth in claim 1 and further, wherein said hydroxycarboxylic acid comprises citric acid.

4. The veterinary composition as set forth in claim 1 and further, wherein said buffering agent comprises ammonium carbonate.

5. The veterinary composition as set forth in claim 1 and further, wherein said simple copper (II) salt comprises copper sulfate pentahydrate, said hydroxycarboxylic acid comprises citric acid, and said buffering agent comprises ammonium carbonate.

6. The veterinary composition as set forth in claim 1 and further, wherein said simple copper (II) salt is selected from the group consisting of a copper (II) halide, copper (II) acetate, copper (II) acetylacetonate, copper (II) carbonate, copper (II) citrate, copper (II) lactate, copper (II) tartrate, copper (II) gluconate, copper (II) glycolate, copper (II) diisopropylsalicylate, copper (II) tetraflouroborate, copper (II) hexafluoroantimonate, copper (II) methoxide, copper (II) nitrate, copper (II) perchlorate, copper (II) thiocyanate, copper (II) trifluoromethanesulfonate, copper (11) molybdate, and copper (II) tungstate, or combinations thereof.

7. The veterinary composition as set forth in claim 6 and further, wherein said simple copper (II) salt is selected from the group consisting of a simple copper (I) salt which upon dissolution in water under an atmosphere of air oxidizes to form one of said simple copper (II) salts.

8. The veterinary composition as set forth in claim 1 and further, wherein said hydroxycarboxylic acid is selected from the group consisting of homocitric acid, lactic acid, gluconic acid, ascorbic acid, and tartaric acid.

9. The veterinary composition as set forth in claim 1 and further, wherein said hydroxycarboxylic acid is selected from the group consisting of a hydroxyacid with $\alpha$, $\beta$, $\gamma$, or $\delta$ hydroxy substitution.

10. The veterinary composition as set forth in claim 1 and further, wherein said hydroxycarboxylic acid is selected from the group consisting of a hydroxyacid having one or more carboxylic acid and hydroxyl functional groups.

11. The veterinary composition as set forth in claim 1 and further, wherein said buffering agent is selected form the group consisting of a simple ammonium salt, a simple carbonate salt, and a combination of a simple ammonium salt and a simple carbonate salt.

12. The veterinary composition of claim 1 wherein said therapeutically effective dosage is effective for reducing the incidence and magnitude of viral and bacterial based diarrhea related disorders in poultry and swine.

13. A method of reducing the incidence and magnitude of diarrhea disorders in poultry and swine, comprising the steps of:
   (a) providing approximately equal portions (weight) of a simple copper (II) salt and a hydroxycarboxylic acid along with a minor amount of a buffering agent;
   (b) dissolving said simple copper (II) salt, said hydroxycarboxylic acid, and said buffering agent in a quantity of water sufficient to produce a therapeutic veterinary solution; and
   (c) supplying said therapeutic veterinary solution to the drinking water of one of said poultry and said swine at a therapeutically effective rate.

14. The method as set forth in claim 13 and further, said step (a) including the further sub-step of providing said simple copper (II) salt as copper sulfate pentahydrate.

15. The method as set forth in claim 13 and further, said step (a) including the further sub-step of providing said hydroxycarboxylic acid as citric acid.

16. The method as set forth in claim 13 and further, said step (a) including the further sub-step of providing said buffering agent as ammonium carbonate.

17. The method as set forth in claim 13 and further, said step (a) including the further sub-steps of (i) providing said simple copper (II) salt as copper sulfate pentahydrate; (ii) providing said hydroxycarboxylic acid as citric acid; and (iii) providing said buffering agent as ammonium carbonate.

18. The method as set forth in claim 13 and further, said step (c) including the further sub-step of providing said therapeutic veterinary solution to said drinking water of said poultry and swine at a therapeutically effective rate of 1 part by volume therapeutic veterinary solution to between 750 and 1000 parts by volume drinking water for 50% to 100% of the time.

19. The method as set forth in claim 13 and further, said step (c) including the further sub-step of providing said therapeutic veterinary solution to said drinking water of said poultry and swine at a therapeutically effective rate of 1 part by volume therapeutic veterinary solution to between 250 and 750 parts by volume drinking water for 100% of the time.

20. The method of claim 13, wherein said method reduces the incidence and magnitude of viral and bacterial based diarrhea related disorders in poultry and swine.

21. A method of mitigating the incidence and effects of a plurality of diarrhea related disorders in poultry and swine, comprising the steps of:
   (a) codissolving amounts of a simple copper (II) salt, a hydroxycarboxylic acid, and a buffering agent in water to produce a therapeutic veterinary solution; and
   (b) administering a therapeutically effective dosage of said therapeutic veterinary solution to the drinking water of one of poultry and swine.

22. The method as set forth in claim 21 and further, said step (a) including the further sub-steps of (i) providing said simple copper (II) salt as copper sulfate pentahydrate; (ii) providing said hydroxycarboxylic acid as citric acid; and (iii) providing said buffering agent as ammonium carbonate.

23. The method as set forth in claim 22 and further, said sub-step (a)(i) including the further sub-step of providing between 113 and 340 grams of said copper sulfate pentahydrate, said sub-step (a)(ii) including the further sub-step of providing between 90 and 340 grams of said citric acid, and said sub-step (a)(iii) including the further sub-step of providing between 2 and 68 grams of ammonium carbonate, and step (a) including the further sub-step (iv) of dissolving said copper sulfate pentahydrate, said citric acid, and said ammonium carbonate within a quantity of water sufficient to form one liter of said therapeutic veterinary solution.

24. The method as set forth in claim 23 and further, said step (b) including the further sub-step of administering said therapeutic veterinary solution to said drinking water at a rate of 1 part by volume therapeutic veterinary solution to between 750 and 1000 parts by volume drinking water for 50% to 100% of the time.

25. The method as set forth in claim 23 and further, said step (b) including the further sub-step of administering said therapeutic veterinary solution to said drinking water at a rate of 1 part by volume therapeutic veterinary solution to between 250 and 750 parts by volume drinking water for 100% of the time.

26. The method as set forth in claim 23 and further, said step (b) including the further sub-step of administering said therapeutic veterinary solution to said drinking water at a rate of 1 part by volume therapeutic veterinary solution to approximately 999 parts by volume drinking water for 50% to 100% of the time.

27. The method as set forth in claim 23 and further, said step (b) including the further sub-step of administering said therapeutic veterinary solution to said drinking water at a rate of 1 part by volume therapeutic veterinary solution to approximately 500 parts by volume drinking water for 100% of the time.

28. The method of claim 21, wherein said method reduces the incidence and magnitude of viral and bacterial based diarrhea related disorders in poultry and swine.

\* \* \* \* \*